Feb. 26, 1957 W. E. SILVA Plant Pat. 1,574

ROSE PLANT

Filed Feb. 14, 1956

WITNESS

Addison F. Avery

INVENTOR

William E. Silva by Rummler, Rummler & Snow

ATTYS.

United States Patent Office

Plant Pat. 1,574
Patented Feb. 26, 1957

1,574

ROSE PLANT

William E. Silva, Sebastopol, Calif., assignor to Peter J. Booy Rose Nursery, San Jacinto, Calif., a partnership consisting of Peter J. Booy and Henry F. Eckardt Application February 14, 1956, Serial No. 565,521

1 Claim. (Cl. 47—61)

Figures 1, 2:
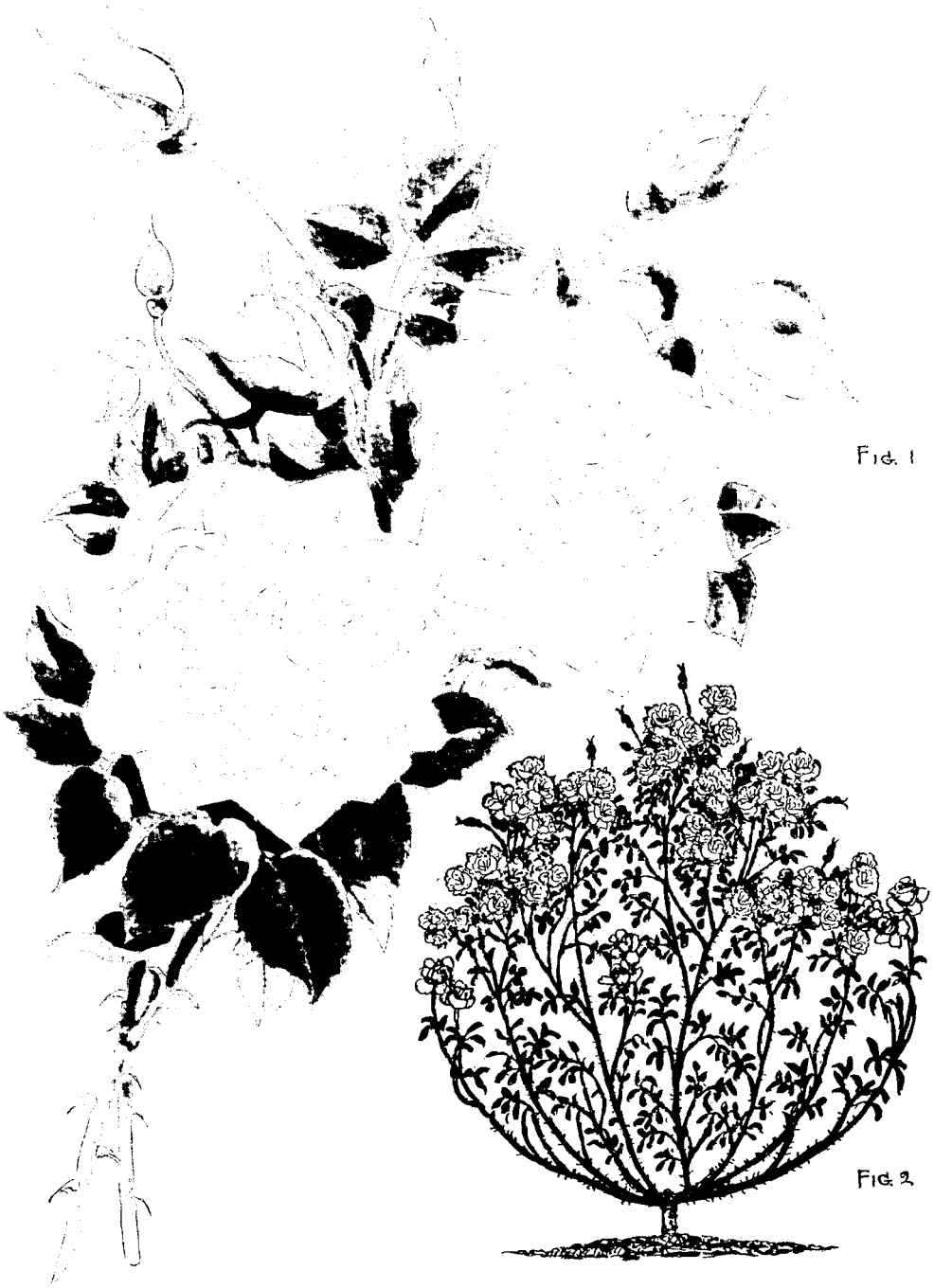

The present discovery concerns a new and distinct variety of rose plant resulting from a cross made by me between the varieties "Duchess of Athol" (unpatented) and "Orange Everglow" (plant Patent 505). My new variety has been reproduced asexually by summer field budding since 1948 at Sebastopol, Calif., and its characteristics appear to be permanently fixed.

The unusual qualities of this new variety reside in its exquisite warm yellow, uniform color, its continuous blooming habit, its disease resistance, and its vigorous, healthy, erect and orderly bushy habit of growth.

At the terminus of the peduncles, this new variety has a profusion of yellow blooms at the peak of the season and plant growth which, combined with the shades of light to dark green leaves, tinges of red on the very young foliage, and reddish hued thorns, make it an outstanding and distinctive rose plant. The blooms are particularly attractive in that the central group of petals stand out prominently and solid.

Trials of the new variety have been conducted in southern California, in a warm dry climate, and the new variety has been carefully tested and observed for more than five years with respect to its growing habits and its resistance to the common rose diseases such as, blackspot, mildew, and canker. The results of these trials and tests have demonstrated that the before-mentioned qualities of the new variety are firmly fixed, and that resistance to common rose diseases is inherent in the new variety.

The nearest resemblance of rose plant to this new variety is "Goldilocks" (Plant Patent #672); but the well-defined differences of the new variety reside in its larger flower, better color, continuous blooming habit, resistance to diseases common to roses, and the uniform rounded forms of the bush. Also, this new variety sheds cleaner than "Goldilocks." In addition to these distinctive differences, the new variety is one of the few yellow floribundas.

In the accompanying drawing, showing the distinctive characteristics of my new variety, Fig. 1 is a view in full color showing the blooms in all stages from bud to full opened flower; and Fig. 2 is a pen and ink sketch illustrative of the form and arrangement of a typical bush or full plant.

Other features of novelty will appear more particularly in the following detailed description of my new rose:

Parentage: Seedling.

*Seed parents.*—"Duchess of Athol."

*Pollen parents.*—"Orange Everglow."

Classification: Floribunda.

Flower:

*Blooming habits.*—Continuously and profusely from spring to fall.

*Size.*—Medium—3 to 3½ inches in diameter.

*Form.*—Rather flat—about 1¼ inches high.

*Borne.*—In clusters.

*Shape.*—Cup-shaped.

*Petalage.*—Approximately 130. Form—oblanceolate to obovate.

*Color.*—Outer petals—yellow to buff. Inner petals—yellow. Base—dark canary yellow. Reverse side—dark yellow.

*Discolorations.*—None.

*Texture.*—Soft.

*Appearance.*—Satiny.

*Affected by wet or hot weather.*—Bleaches in hot weather. Resistant to common diseases of the rose and particularly blackspot, mildew and canker.

*Fragrance.*—Very fragrant, with regular but stronger rose fragrance than that of the parent varieties; and longer lasting fragrance in the cut flowers than either the parent varieties or the variety "Goldilocks."

*Lasting quality.*—On plant—good. As a cut flower—fair.

Bud:

*Size.*—Approximately ½ inch diameter.

*Form.*—Short with flat top. Globular—urn-shaped in form.

*Color.*—When sepals first divide—greenish-yellow with red spots. When petals begin to unfurl—dark canary yellow.

*Sepals.*—Stand up over bud. Turn down when bloom is full.

*Shape.*—Spear-shaped.

*Calyx.*—Shape—long, funnel-shaped. Slightly hairy. Size—long, ⅜ inch. Does not split and is not glandular.

*Peduncle.*—14 inches long. Not hairy.

Plant:

*Form.*—Bush—spreading and rounded.

*Height.*—Approximately 24 inches.

*Growth.*—Vigorous and branching.

*Foliage.*—Abundant. Each spray about 3½ inches long and having 7 leaves. Size of leaf—mature leaves approximately 1 inch wide and 1¼ inches long. Texture—smooth. Color—upper side—dark green; under side—light green; small young leaves have a reddish border and red veins and ribs. Shape—elliptical, serrated. Petioles—length, 2 to 2½ inches.

*Thorns.*—Quite profuse. Size—⅛ to ¼ inch; large large thorns on lower branches. Young thorns—reddish base, green top, pointing down. Older thorns—reddish-brown color, point down more than younger thorns.

Genital organs:

*Stamens, anthers.*—Length—¼ inch. Number—20. Color—filament, green; anther, yellow. Arrangement—circled around pistils. Pollen—yellow.

*Styles.*—Number—70. Length—¼ inch.

*Ovaries.*—Normal.

The color characteristics of my new variety according to "Maerz and Paul's Dictionary of Color" and "British Colour Council Horticultural Colour Chart" are as follows:

| | Plate | Letter | No. |
|---|---|---|---|
| Flower: | | | |
| Lightest yellow: Hort. Colour Chart: 603 Empire Yellow from 603/3 to 603/1 | 9 | K | 5 |
| Deepest Yellow at center: Maerz & Paul—to | 9 | L | 7 |
| Leaves: | | | |
| Smaller newer leaves—upper side | 20 | L | 8 |
| Older large leaves—upper side | 23 | L | 6 |
| Under side of leaves | 21 | K | 4 |
| Thorns | 7 | J | 7 |

Having thus disclosed my discovery, I claim:

A new and distinct variety of rose plant of the floribunda class, substantially as herein shown and described, characterized as to novelty by its vigorous, bushy spreading habit of growth and sturdy stems, by its profuse flowering habit from spring until fall, the distinctive rich yellow coloring of the blooms and compact arrangement of the petals, and its resistance to common rose diseases.

No references cited.